US008705690B2

(12) United States Patent
Jerebko et al.

(10) Patent No.: US 8,705,690 B2
(45) Date of Patent: Apr. 22, 2014

(54) IMAGING METHOD WITH IMPROVED DISPLAY OF A TISSUE REGION, IMAGING DEVICE, AND COMPUTER PROGRAM PRODUCT

(75) Inventors: Anna Jerebko, Erlangen (DE); Klaus Engel, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 19 days.

(21) Appl. No.: 13/358,081

(22) Filed: Jan. 25, 2012

(65) Prior Publication Data

US 2012/0189092 A1 Jul. 26, 2012

(30) Foreign Application Priority Data

Jan. 25, 2011 (DE) .................... 10 2011 003 137

(51) Int. Cl.
*A61B 6/04* (2006.01)
(52) U.S. Cl.
USPC .............................................. 378/37; 378/21
(58) Field of Classification Search
USPC ............................. 378/4, 37, 21–26; 382/131
See application file for complete search history.

(56) References Cited

U.S. PATENT DOCUMENTS

| 5,371,778 | A * | 12/1994 | Yanof et al. ..................... 378/4 |
| 5,986,662 | A * | 11/1999 | Argiro et al. ................. 345/424 |
| 7,760,924 | B2 | 7/2010 | Ruth et al. |
| 7,945,014 | B2 | 5/2011 | Mertelmeier |
| 7,965,812 | B2 | 6/2011 | Hanke et al. |
| 2004/0081273 | A1 * | 4/2004 | Ning ................................ 378/37 |
| 2004/0228453 | A1 * | 11/2004 | Dobbs et al. ................. 378/210 |
| 2006/0004278 | A1 * | 1/2006 | Giger et al. ................... 600/408 |
| 2008/0019581 | A1 * | 1/2008 | Gkanatsios et al. ......... 382/131 |
| 2008/0101536 | A1 * | 5/2008 | Sendai .......................... 378/22 |
| 2008/0130979 | A1 * | 6/2008 | Ren et al. ..................... 382/132 |
| 2009/0034684 | A1 | 2/2009 | Bernard et al. |
| 2009/0080752 | A1 | 3/2009 | Ruth et al. |
| 2009/0123052 | A1 * | 5/2009 | Ruth et al. ................... 382/132 |
| 2009/0310844 | A1 | 12/2009 | Ludwig et al. |
| 2010/0034450 | A1 | 2/2010 | Mertelmeier |
| 2010/0086188 | A1 | 4/2010 | Ruth et al. |
| 2010/0166267 | A1 * | 7/2010 | Zhang et al. ................. 382/128 |
| 2011/0122992 | A1 | 5/2011 | Hanke et al. |
| 2011/0216879 | A1 | 9/2011 | Jing et al. |
| 2012/0114095 | A1 * | 5/2012 | Smith et al. .................... 378/20 |

FOREIGN PATENT DOCUMENTS

| DE | 102006046741 A1 | 4/2008 |
| DE | 102008004473 A1 | 7/2009 |
| DE | 102008028387 A1 | 12/2009 |
| DE | 102008033150 A1 | 2/2010 |
| EP | 1925255 A1 | 5/2008 |
| EP | 2138098 A1 | 12/2009 |

OTHER PUBLICATIONS

Arnulf Oppelt, "Imaging Systems for Medical Diagnostics", Book, 2005, pp. 47-48, Publicis Corporate Publishing, Erlangen, Germany.
German Patent and Trademark Office, Office Action, Dated Jul. 4, 2011.

* cited by examiner

*Primary Examiner* — Hoon Song
(74) *Attorney, Agent, or Firm* — Laurence A. Greenberg; Werner H. Stemer; Ralph E. Locher

(57) ABSTRACT

An imaging method with an improved display of a tissue region generates a first visualization and a second visualization from projection recordings that were recorded at different angles. A radiologist is enabled to mark a region in the first visualization, which region is displayed by way of the second visualization.

14 Claims, 4 Drawing Sheets

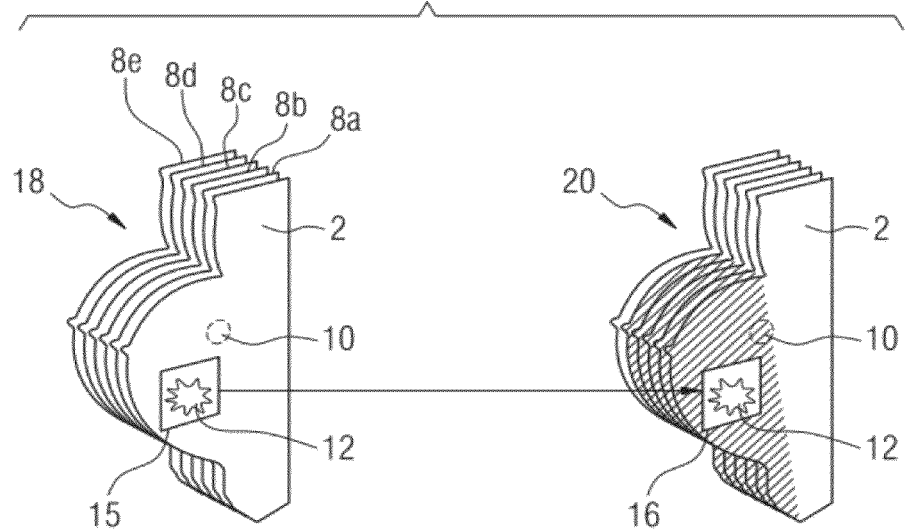
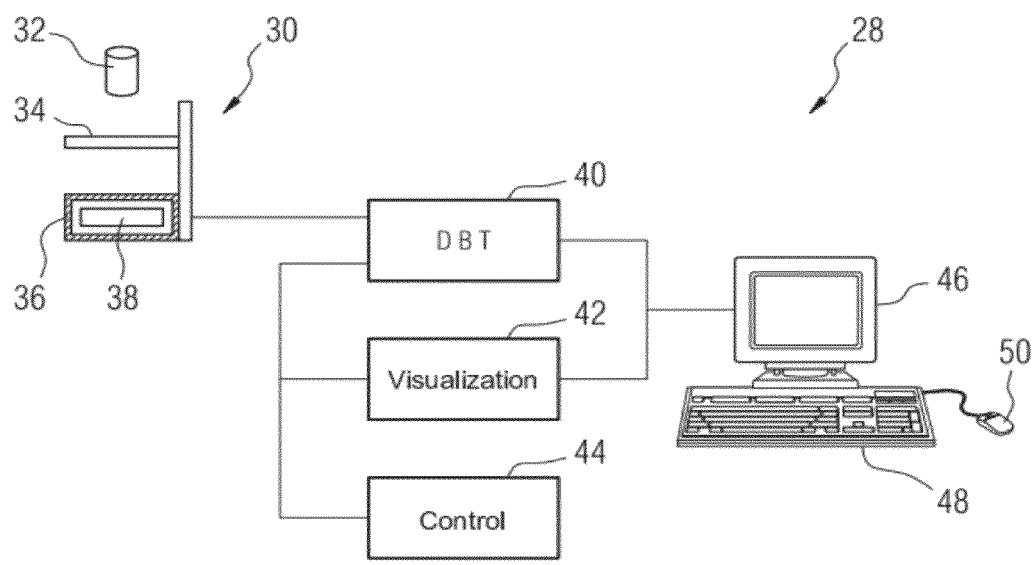

IMAGING METHOD WITH IMPROVED DISPLAY OF A TISSUE REGION, IMAGING DEVICE, AND COMPUTER PROGRAM PRODUCT

CROSS-REFERENCE TO RELATED APPLICATION

This application claims the priority, under 35 U.S.C. §119, of German patent application DE 10 2011 003 137.5, filed Jan. 25, 2011; the prior application is herewith incorporated by reference in its entirety.

BACKGROUND OF THE INVENTION

Field of the Invention

The present invention relates to an imaging method, more particularly a mammography method, in which a tissue region is displayed in an improved fashion.

In a tomosynthesis process, a three-dimensional image is generated from a plurality of two-dimensional projections. An X-ray apparatus with an X-ray beam source and a detector is used to generate a first two-dimensional image or a first projection of the tissue to be examined, through which tissue the X-ray beam passes. Here, the two-dimensional image represents the attenuation of the X-ray radiation by the tissue in the volume or in the breast. A second two-dimensional image or a second projection of the same tissue or volume is recorded after the beam source and/or the detector was moved into a second position. After a plurality of two-dimensional images were recorded, a three-dimensional tomosynthesis image can be generated by means of a reconstruction.

Mammography is a field of application of the three-dimensional imaging method mentioned above. An image generation device typically used in mammography comprises a pivotable X-ray beam source and a stationary X-ray detector. The tissue to be examined is positioned over the stationary detector, with the tissue to be examined being compressed and not being in a natural shape. The X-ray source is subsequently pivoted over a number of steps or continuously, for example within a range of +/−25°, and the stationary detector is used to record a plurality of two-dimensional X-ray images from different pivot positions of the X-ray beam source. It goes without saying that it is also possible to use a plurality of stationary X-ray beam sources or to merely displace the X-ray beam source in a translational fashion. It is also possible for the detector to be displaced or pivoted counter to the movement of the X-ray source. In the case of craniocaudal recordings, the X-ray beam source(s) emit(s) X-ray beams from positions that are arranged along a line running parallel to the axis running from shoulder to shoulder of the patient. A beam path parallel to the chest wall can result in the entire tissue of the breast being imaged and the thorax not being irradiated. A three-dimensional image is generated from the plurality of two-dimensional X-ray images by means of the reconstruction.

Pertinent prior art imaging methods and devices for mammography are described, for example, in the following commonly assigned patents and published patent applications: U.S. Pat. No. 7,945,014 B2 and DE 10 2006 046 741 A1; US 2010/0034450 A1 and DE 10 2008 004 473 A1; US 2011/0122992 A1 and DE 10 2008 033 150 A1; U.S. Pat. No. 7,965,812 B2 and EP 2 138 098 A1; and US 2009/0310844 A1 and DE 10 2008 028 387 A1.

In the prior art, so-called filtered back projections are used to reconstruct a three-dimensional image from a plurality of two-dimensional images; by way of example, these filtered back projections are described in chapter 10.5 of Imaging Systems for Medical Diagnostics, Arnulf Oppelt, Publicis Corporate Publishing, Erlangen, ISBN 3-89578-226-2. These filtered back projection reconstruction methods display reconstructed images with a comparatively high contrast and comparatively great detail, but lose information in respect of the relative tissue density in the case of tomosynthesis with a restricted scanning angle as a result of the missing data. This is the result of certain filter kernels removing low-frequency components. In general, digital breast tomosynthesis (DBT) is afflicted by incomplete data and poor quantum statistics, which is restricted by the overall dose absorbed in the breast. The breast mainly consists of glandular tissue, fatty tissue, connective tissue and blood vessels. The X-ray attenuation coefficients of these types of tissue are very similar, making the evaluation of three-dimensional mammography images significantly harder. The main field of application of imaging methods in mammography is the early detection of cancerous tissue. This is made more difficult by the fact that cancerous tissue has a similar X-ray attenuation coefficient to other types of tissue.

By way of example, mammography methods are described in chapter 12.6 of Imaging Systems for Medical Diagnostics, Arnulf Oppelt, Publicis Corporate Publishing, Erlangen, ISBN 3-89578-226-2.

In the prior art, a so-called slab-MIP (slab maximum intensity projection), an average intensity projection rendering, a multiple planar reconstruction (MRP), a maximum intensity projection (MIP) or simply a generated two-dimensional mammography image, which was generated from the tomosynthesis projection images and/or from the reconstructed tomosynthesis image data, is used for visualizing tomosynthesis data. As a result of the density of the data and the occlusion resulting therefrom, these techniques are not suitable for analyzing soft-tissue data. High density soft tissue can only be visualized by removing the occluding low density soft tissue, for example by means of an opacity transfer function. It follows that the low density tissue, which provides important context information for the features with a high density, is no longer present in the visualization. This is undesirable when examining soft tissue because the soft-tissue contrast provides the main source of information for diagnosing tissue changes.

SUMMARY OF THE INVENTION

It is accordingly an object of the invention to provide an imaging process which overcomes the above-mentioned disadvantages of the heretofore-known devices and methods of this general type and which provides for an improved display of a tissue region in that a tissue volume is imaged such that a tissue change can be identified in an improved manner.

With the foregoing and other objects in view there is provided, in accordance with the invention, an imaging method, which comprises:

generating a plurality of projection recordings and thereby, for each of the projection recordings, emitting radiation into a tissue region at a respectively different angle with at least one emitter and capturing the radiation with a detector;

generating a first visualization from the projection recordings by way of a first visualization method; and generating a second visualization from the projection recordings by way of a second visualization method.

In other words, the objects of the invention are achieved by an imaging method that generates a plurality of projection recordings, wherein, for each projection recording, radiation is emitted into a tissue region at a different angle by at least one emitter, which radiation is captured by a detector. A first visualization is generated from the projection recordings by means of a first visualization method. A second visualization is generated from the projection recordings by means of a second visualization method.

The first visualization is displayed on a display apparatus, for example a monitor. The radiologist can select a region in the first visualization. The selected region is displayed by way of the second visualization. The radiologist can diagnose the tissue region by means of the first visualization. If a specific region should be examined in more detail, this region can be marked. This region is subsequently displayed by means of the second visualization. Since the first visualization and the second visualization differ from one another, the region can be displayed in a different fashion, and so the radiologist obtains additional information. This can reduce false positive diagnoses and false negative diagnoses.

The first visualization and the second visualization can be calculated and stored before being displayed. The visualizations can preferably be stored on a hard disk drive. Hence the visualizations can be pre-calculated after the X-ray and be stored before being displayed. This reduces the load on a computer when displaying the visualization. Therefore, the radiologist can examine the first visualization and the second visualization, and hence the tissue region, without waiting times arising because a visualization has to be calculated anew. It is understood that more than two visualizations can be pre-calculated and stored.

The second visualization can be superposed on the first visualization in the selected region. As a result, this ensures a reliable spatial association between the first visualization and the second visualization.

The first visualization method can be a reconstruction method for generating slice images. The reconstruction method can comprise a back projection method. The second visualization method can comprise a method for generating at least one projection image. The projection image is preferably generated using a forward projection method. Hence the radiologist can examine the tissue region by means of the slice images. The radiologist can use the projection image to examine a tissue region of particular interest. Since a projection image simulates an X-ray beam passing through a tissue region, a tissue change is displayed with particularly high contrast since the simulated X-ray beam is damped over the whole length of the tissue change. This affords the possibility of forming higher-contrast images of a tissue change, which cannot be identified as well in a slice image recording.

The invention is advantageous in that, firstly, a tissue change can be localized precisely and, secondly, it can be displayed with a high contrast. The first visualization method allows the precise localization of the tissue change by means of the slice images. The second visualization method allows a high-contrast representation by the projection image. The projection image can be generated by means of a maximum intensity projection (MIP), an average intensity projection (AIP), etc.

During the generation of the projection image, merely one part of the volume reconstructed by the first visualization method can be used for generating the at least one projection image. In this case, use can be made of techniques such as "slab MIP" or "slab AIP".

The second visualization method can include the step of rotating at least one part of the first visualization and/or the step of rotating at least one part of the first visualization and generating a projection image from the rotated first visualization. A second visualization can constitute a slice image that emerges when a plane in the reconstructed image volume is rotated. It is also possible to generate a projection image that simulates a rotating X-ray source.

The second visualization can have a higher resolution than the first visualization. The second visualization can display a different grayscale value range than the first visualization. By way of example, the first visualization could visualize a grayscale value range in which soft tissue parts are visible particularly well. The second visualization can have a grayscale value range in which calcifications are displayed particularly well.

The most suitable way of observing the mass tissue of the breast is using the reconstructed slice images; however, these are not always optimal for identifying calcified clusters. While the first visualization includes the reconstructed slice images, the second visualization can include rotating MIPs or a rotating simulated mammogram. In the second visualization, the radiologist is able to observe calcified clusters from different angles. In the first visualization, clicking the mouse enables the radiologist to open a window in which the second visualization is displayed. If the cursor is moved within the window for the second visualization, the rotating mammogram is turned or the rotating MIP representation is turned, while the first visualization remains stationary. If the cursor is moved within the first visualization, the first visualization is shifted by displaying other slice images, and the second visualization is not moved, i.e. the rotating mammogram or the rotating MIP does not turn.

A movable window can be displayed over the first visualization. The second visualization can be displayed in the movable window. The second visualization is updated on the basis of a modified position of the movable window. The radiologist can move the movable window over the first visualization, with the respective second visualization of the region marked by the window being displayed within the window. Hence the radiologist can examine in detail a tissue region by means of two different visualizations in a comparatively short time. The window can be moved over the first visualization like a magnifying glass.

With the above and other objects in view there is also provided an imaging method in the form of a mammography method.

With the above and other objects in view there is also provided, in accordance with the invention, a visualization device which is designed to carry out the above-described method. The invention also discloses an imaging system with the visualization device.

Finally, the invention also provides for a computer program product which can be or is loaded into a memory of a computer and comprises computer-executable program code designed to carry out the above-described method.

Other features which are considered as characteristic for the invention are set forth in the appended claims.

Although the invention is illustrated and described herein as embodied in an imaging method with an improved display of a tissue region, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 6 schematically shows the representation of the first visualization and the second visualization; and FIG. 7 shows an imaging system according to the invention.

DETAILED DESCRIPTION OF THE INVENTION

The invention will be explained below with reference to mammography. It is understood that the invention is also applicable to other fields.

Figure 1:
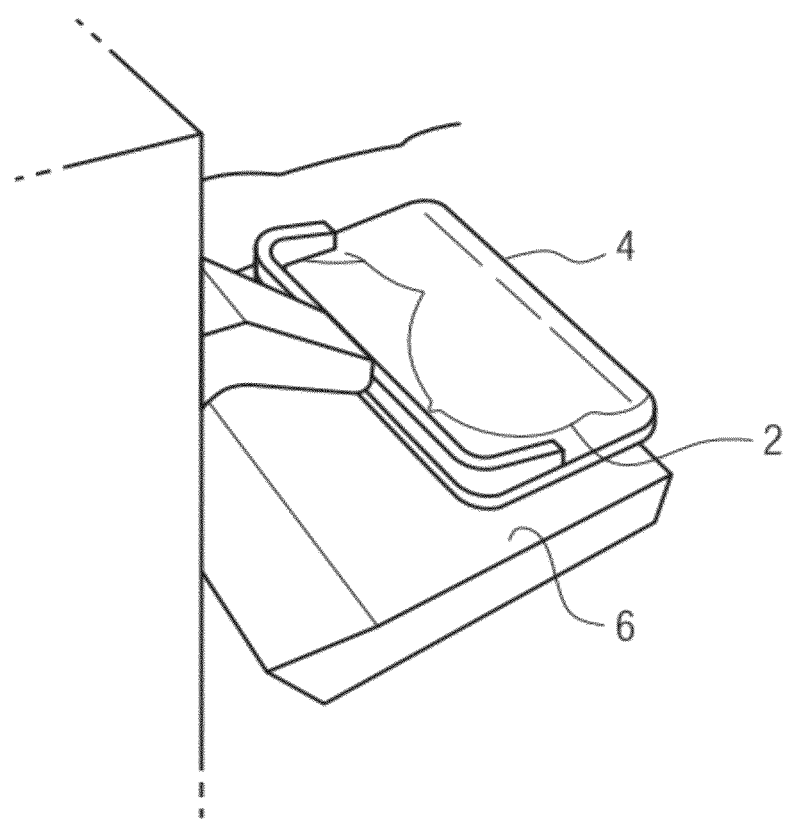
FIG. 1 shows a modality, in which the breast is compressed in order to carry out recordings of the interior of the breast.

Referring now to the figures of the drawing in detail and first, particularly, to FIG. 1 thereof, there is shown a first imaging modality, which has a compression plate 4 and a compression table 6, between which the breast 2 is clamped. The breast is usually compressed in this fashion until a predetermined compression force is reached. A plurality of X-ray sources or at least one movable X-ray source (not illustrated) can be arranged over the compression plate 4. An X-ray detector can be arranged in or below the compression table 6. This device can be used to capture projections from different directions by means of X-ray radiation, from which, as described at the outset, it is possible to generate slice images.

The compressed breast is captured in the mediolateral oblique (MLO) position in the first imaging modality 1.

The method for generating the projections is explained with reference to FIG. 2. A plurality of X-ray sources 102, 104, 106 are arranged over an angular range of approximately 50°. It is possible for 25 X-ray sources to be arranged, and so 25 projections can be generated. As an alternative to this, it is possible for an X-ray source to be pivoted over an angular range of 50° such that 25 projection recordings are generated. The first X-ray source 102 emits a first X-ray beam 108, which passes through the breast 114 and is attenuated by a first tissue region 116, a second tissue region 118 and a third tissue region 120. An X-ray detector 128 generates a first projection recording 130, in which the first tissue region image 122, the second tissue region image 124 and the third tissue region image 126 are in a first arrangement. The second X-ray beam source 104 emits a second X-ray beam 110, at a different angle, to the breast 114, the first tissue region 116, the second tissue region 118 and the third tissue region 120. These tissue regions are recorded by the second projection recording 132 and are in an arrangement that differs from that of the first slice recording 130. The third X-ray source 106 emits a third X-ray beam 112 to the breast at a further angle and this beam generates a third arrangement of the first tissue region image 122, second tissue region image 124 and third tissue region image 126 in the third projection recording 134.

Figure 3:
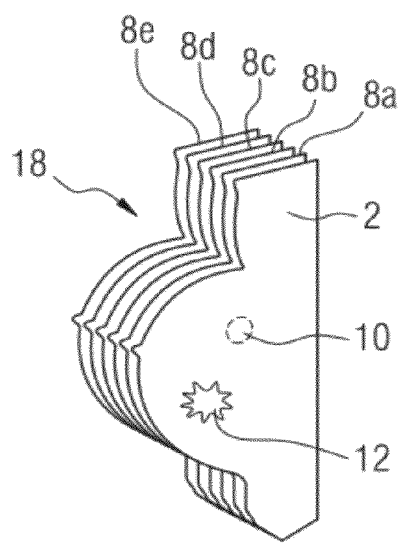
FIG. 3 schematically shows a first visualization of the breast tissue.
Figure 4:
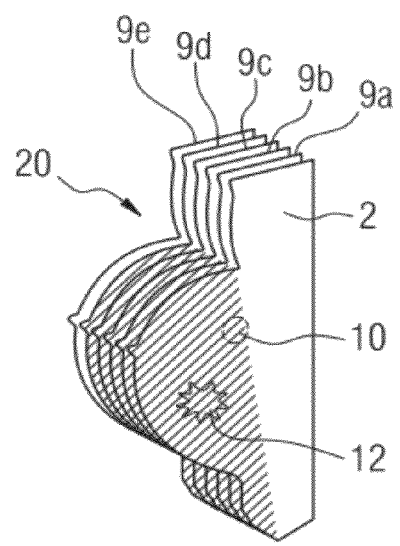
FIG. 4 shows a second visualization of the breast tissue.

FIG. 3 shows a first visualization 18 of the breast 2 in the form of a plurality of slice images 8a to 8e. Furthermore, a first tissue change 10 and a second tissue change 12 are illustrated in the first visualization. FIG. 4 schematically shows a second visualization 20 of the tissue region in the form of projections 9a to 9e. It is also possible to identify the breast tissue 2, the first tissue change 10 and the second tissue change 12 in the second visualization.

Figure 2:
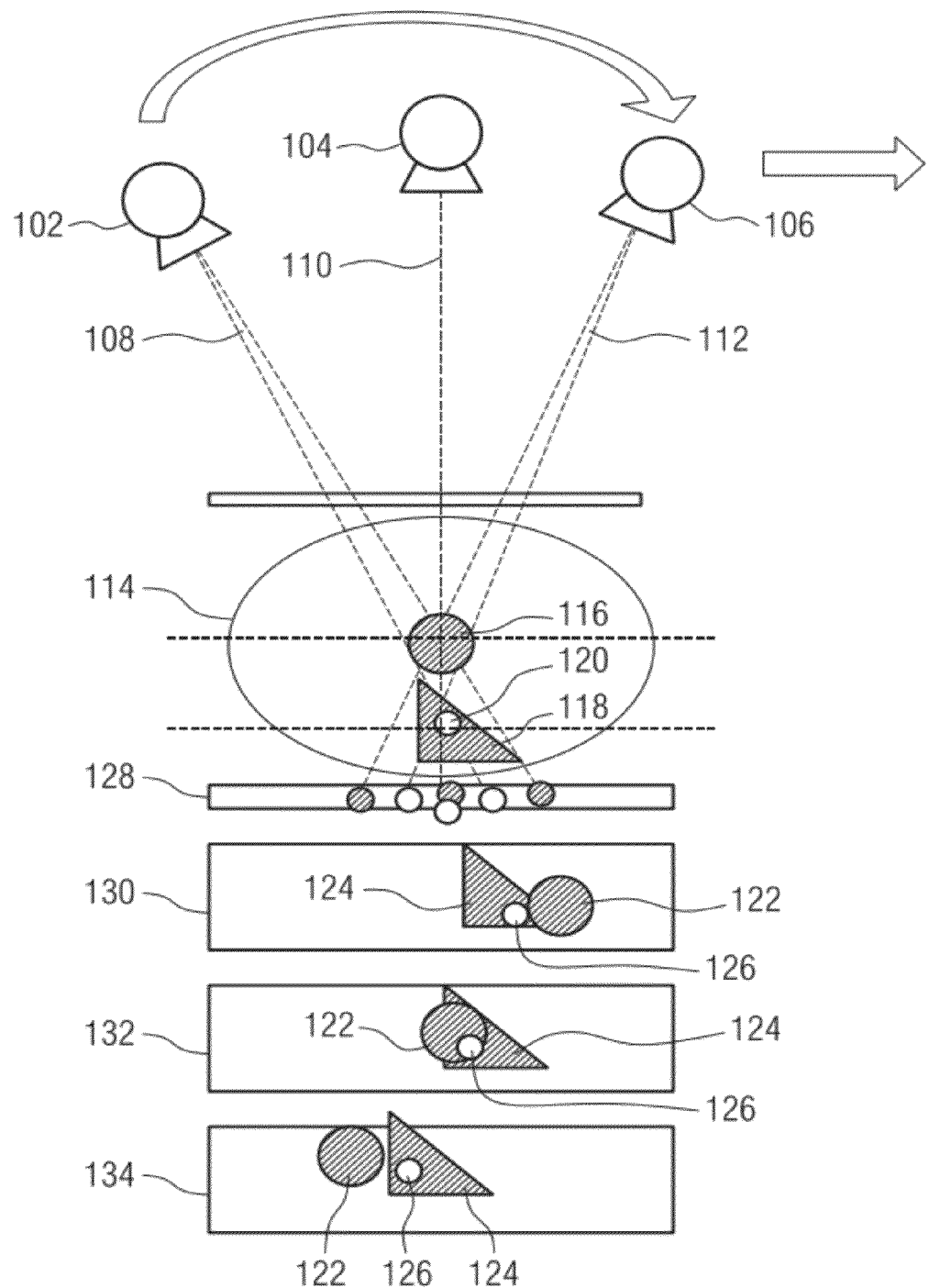
FIG. 2 schematically shows a tomosynthesis being carried out.

The first visualization 18 and the second visualization 20 are generated after capturing the projection recordings as per the method described in FIG. 2 and are stored in a non-volatile memory, for example a hard disk drive. If use is made of more than two visualizations, all visualizations can be calculated and stored after generating the projection recordings as per the method described in relation to FIG. 2. All visualizations are calculated before being displayed on a display apparatus, for example a monitor. It follows that the visualizations can be displayed on the display apparatus at a suitable speed and the display apparatus does not require a powerful processor. Hence the visualizations are calculated and stored before being displayed.

Figure 5:
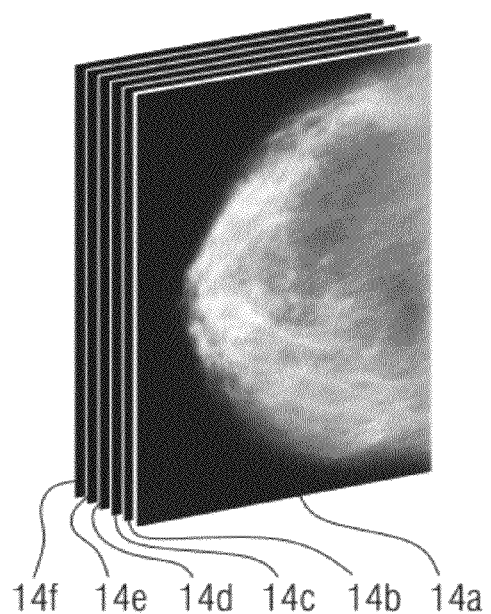
FIG. 5 shows slice images produced by means of DBT.

FIG. 5 shows a plurality of slice images, which were generated by means of the imaging modality, i.e. by means of DBT, and form the first visualization of the breast 16. A plurality of slice images 14a to 14f are shown. Since cancerous breast tissue has a similar attenuation coefficient to healthy tissue, it is difficult to assess whether cancerous tissue is present. This results in false positive or false negative diagnoses.

Reference is now had to FIG. 6.

The radiologist navigates through the slice images 8a to 8e of the first visualization 18. The radiologist can identify the second tissue change 12 in this representation. However, the contrast in the first visualization 18 may not be sufficient for assessing whether there is a pathological tissue change. Therefore the radiologist is able to mark a region 15 in which the second tissue change is situated. Now a window 16 is opened and it displays the region 15 by means of the second visualization 20.

The second visualization 20 can constitute a projection. The projection can have a higher contrast because the projection simulates an X-ray beam that passes through the tissue change over a longer path. The second visualization 20 can be calculated by means of a maximum intensity projection, an average intensity projection, a "slab-MIP", "slab-AIP", etc. Furthermore, the second visualization 20 can have a rotating slice image or a rotating projection, which was calculated using the aforementioned method. The maximum intensity projection and the average intensity projection simplify the diagnosis of the distribution of calcification clusters. The second visualization 20 can be a reconstruction that, like the first visualization 18, was reconstructed from the projection images but by using a different method. The second visualization 20 can have simulated three-dimensional rotating mammograms or recorded two-dimensional mammograms.

The second visualization 20 can also have a volume that was reconstructed with a higher resolution. The second visualization 20 can also have an image or a reconstruction, respectively recorded or created at an earlier time, of the same breast. It follows that the radiologist can alternate between two visualizations that were recorded at different times. As a result, it is possible to check changes over time in a particularly good fashion.

The second visualization 20 may have at least one item of image information that was generated as described above. However, it is also possible that the second visualization can have a plurality of different items of image information. Therefore the radiologist is able to display different visualizations in a region of particular interest, as a result of which the diagnosis can be made more easily. In particular, the radiologist is able to use the visualization that displays the tissue change, for example the cancerous tissue, with the greatest possible contrast with respect to the other breast tissue.

Since the first visualization and the second visualization(s) are calculated and stored before being displayed, the radiologist is able to navigate quickly through the tissue, without waiting times arising when a new visualization is opened.

The second visualization can have a set of maximum intensity projection images or average intensity projection images of the original volume, which display the breast tissue in a pre-calculated set of observation angles. A small angle of rotation, of the order of the angle through which the beam is pivoted during tomosynthesis, is used to avoid the occurrence of artifacts, in particular so-called "out-of-plane artifacts", as a result of the incomplete angular range when pivoting the X-ray beam during DBT. It is understood that the order or arrangement of the first and second visualization can be modified according to the preferences of the radiologist.

The second visualization can be stored as a set of images in the DICOM (digital imaging and communications in medicine) format, a JPEG format, a TIFF format, a BMP format or in another image format.

The workflow when navigating through a volume of digital breast tomosynthesis data can be carried out such that the original slice images are viewed in sequence within the meaning of a first visualization. A zoom window is opened, within which the second visualization is displayed. Within the zoom window, the volume data can be displayed as "window-leveled" maximum intensity projections or as direct volume rendering using multi-dimensional transfer functions. The rotating maximum intensity projection or the rotating average intensity projection could be used for localizing and analyzing calcification cluster distributions in addition to the tomosynthesis slice images, where the calcifications are subdivided into different slice images or viewing planes. Calcifications may be maintained in the second visualization by selecting a suitable grayscale value window (windowing) or a suitable transfer function within the zoom window.

If the zoom window is moved over the volume data within the meaning of a first visualization, the calcifications within the dense soft tissue can be made visible within the magnifying glass as second visualization. This allows a user to analyze how the calcifications are embedded in the surrounding soft tissue. Since the plurality of visualizations are calculated before being displayed, the second visualization can be updated within a short period of time.

Control elements can be provided for the user in order to navigate through the slices of the first visualization and/or the second visualization during the analysis. Moreover, provision can be made for control elements for individually setting the windowing of the grayscale value range, for example for the first visualization, the visualization shown in the zoom window and/or the second visualization. Here, it is possible to set the offset, the width and/or the gradient of the grayscale value range selected, by the window, for the second visualization in an individual fashion and independently of the first visualization.

It is understood that the zoom window can have any shape; by way of example, the zoom window can be spherical, round, for example a cylinder orthogonal to the observation plane, conical or rectangular. The zoom window, in which the second visualization is displayed, can be moved over the first visualization. As a result, the radiologist can diagnose changed tissue in a particularly simple fashion.

By way of example, the control elements can be operated by a conventional computer mouse, wherein the mouse can be used to define the zoom window. Furthermore, pop-up windows can be provided, which can be activated by means of the mouse buttons and by means of which the desired view can be selected. The direction in which the mouse is moved can determine which views are modified. By way of example, a vertical movement of the mouse can be assigned to navigating through the first visualization and a horizontal movement of the mouse can move the second visualization. Moreover, scroll elements on the lower edge and/or on the side edge of the monitor display may be provided and these allow the radiologist to be able to navigate through the visualizations.

The invention is advantageous in that it is possible to navigate through DBT data by visualizing a volume to be analyzed by means of at least two different visualizations. The first visualization can have conventional or original slice recordings, through which the radiologist can navigate in sequence. The radiologist can open a zoom window in which a second visualization is displayed. In the second visualization it is possible to display clearly calcifications or changed tissue, which show additional information in respect of their position or relation to important features such as vessels and masses.

The first visualization 18 and the second visualization 20 can be displayed on the display apparatus 46 as a reaction to a user input.

FIG. 7 shows an imaging system 28 for a medical system. The imaging system 28 comprises an imaging modality 30 with an X-ray beam source 32, a compression plate 34, a compression table 36 and an X-ray detector 38. The X-ray source 32 can be arranged in a pivotable fashion in order to generate projection recordings from different angles, which are captured by means of the X-ray detector 38.

The projections recorded by the X-ray detector 38 are transmitted to a DBT apparatus 40, where slice recordings are generated that are displayed on the display apparatus 46. A control apparatus 44 can, independently or in conjunction with the DBT apparatus 40, establish changed tissue, which is also displayed on the display apparatus 46. The changed tissue can have cancerous tissue, a carcinoma, a lump or any other medically relevant diagnosis. A radiologist can display the changed tissue by means of the input apparatus 48, 50 such that the diagnosis can be made as precisely as possible. The visualization apparatus 42 can generate and store the first visualization 18 and the second visualization 20 from data supplied by the DBT apparatus 40. The control apparatus 44 controls the operation of both the DBT apparatus 40 and that of the visualization apparatus 42.

Finally, reference is made to the fact that the description of the invention and the exemplary embodiments should not, in principle, be understood as being restrictive in view of a particular physical implementation of the invention. More particularly, a person skilled in the art considers it obvious that the invention can be wholly or partly implemented as software and/or hardware, and/or can be implemented distributed over a plurality of physical products—more particularly also computer program products in this case.

The following list of reference numerals used in the above specification may aid the reader in reading the description:

2 Breast
4 Compression plate
6 Table
8 Slice images
9 Projections
10 First tissue change
12 Second tissue change
14 Slice images
15 Marked region
16 Window 18 First visualization
20 Second visualization
28 Medical system
30 Modality
32 X-ray beam source
34 Compression plate
36 Compression table
38 X-ray detector
40 DBT apparatus
42 Visualization apparatus
44 Control apparatus
46 Display apparatus
50 Input apparatus
102 First X-ray source
104 Second X-ray source
106 Third X-ray source
108 First X-ray beam
110 Second X-ray beam
112 Third X-ray beam
114 Breast
116 First tissue region
118 Second tissue region
120 Third tissue region
122 First tissue region image
124 Second tissue region image
126 Third tissue region image
128 Detector
130 First projection recording
132 Second projection recording
134 Third projection recording

The invention claimed is:

1. An imaging method, which comprises:
generating a plurality of projection recordings and thereby, for each of the projection recordings, emitting radiation into a tissue region at a respectively different angle with at least one emitter and capturing the radiation with a detector;
generating a first visualization from the projection recordings by way of a first visualization method being digital breast tomosynthesis (DBT);
generating a second visualization from the projection recordings by way of a second visualization method;
storing the first visualization and the second visualization;
subsequently displaying the first visualization, selecting a region in the first visualization and displaying the selected region by way of the second visualization in a movable window over the first visualization; and
updating the second visualization based on a modified position of the movable window displaying the second visualization.

2. The imaging method according to claim 1, which comprises superimposing the second visualization on the first visualization in the selected region.

3. The imaging method according to claim 1, wherein the first visualization method is a reconstruction method for generating slice images.

4. The imaging method according to claim 1, wherein the second visualization method is a method for generating at least one projection image.

5. The imaging method according to claim 4, which comprises generating the at least one projection image with only a portion of a volume reconstructed by the first visualization method.

6. The imaging method according to claim 1, wherein the second visualization method includes a step of rotating at least one part of the first visualization and/or a step of rotating at least one part of the first visualization and generating a projection image from the rotated first visualization.

7. The imaging method according to claim 1, wherein a resolution of the second visualization is higher that a resolution of the first visualization.

8. The imaging method according to claim 1, which comprises displaying with the second visualization a different grayscale value range than with the first visualization.

9. A visualization apparatus, comprising:
an emitter for emitting radiation and a detector for capturing the radiation configured for carrying out the method according to claim 1.

10. An imaging system, comprising the visualization apparatus according to claim 9.

11. A computer program product, comprising computer-executable code in non-transitory form to be loaded into, or loaded in, a memory of a computer, and configured to carry out the steps of the method according to claim 1 upon being executed on the computer.

12. The imaging method according to claim 1, which comprises generating the second visualization in the movable window to appear as a zoomed magnification of a corresponding region in the first visualization underlying the movable window.

13. A mammography method, which comprises:
emitting radiation into a breast tissue region at respectively different angles from at least one emitter and capturing the radiation with a detector to thereby generate a plurality of projection recordings;
generating a first visualization from the projection recordings by way of a first visualization method;
generating a second visualization from the projection recordings by way of a second visualization method being digital breast tomosynthesis (DBT);
storing the first visualization and the second visualization;
subsequently displaying the first visualization;
selecting a region in the first visualization and displaying the selected region by way of the second visualization in a movable window over the first visualization; and
updating the second visualization based on a modified position of the movable window.

14. The mammography method according to claim 13, which comprises generating the second visualization in the movable window to appear as a zoomed magnification of a corresponding region in the first visualization underlying the movable window.

* * * * *